United States Patent
Barrault et al.

(10) Patent No.: US 6,828,451 B2
(45) Date of Patent: Dec. 7, 2004

(54) METHOD FOR PREPARING A FATTY SUBSTANCE ESTER AND USE THEREOF IN PHARMACEUTICS, COSMETICS OR FOOD INDUSTRY

(75) Inventors: JoëBarrault, Liguge (FR); Mickaël Boisseau, Blaslay (FR); Yannick Pouilloux, Mignoloux-Beauvoir (FR); Antoine Piccirilli, Epernon (FR)

(73) Assignee: Laboratoires Expanscience, Courbevoie (FR)

( * ) Notice: Subject to any disclaimer, the term of this patent is extended or adjusted under 35 U.S.C. 154(b) by 0 days.

(21) Appl. No.: 10/333,467

(22) PCT Filed: Jul. 18, 2001

(86) PCT No.: PCT/FR01/02340

§ 371 (c)(1),
(2), (4) Date: Jan. 21, 2003

(87) PCT Pub. No.: WO02/06205

PCT Pub. Date: Jan. 24, 2002

(65) Prior Publication Data

US 2003/0195367 A1 Oct. 16, 2003

(51) Int. Cl.$^7$ .......................... C07C 53/00; C07C 57/00; C07C 69/74; C07C 69/00
(52) U.S. Cl. ............................ 554/1; 554/124; 554/174; 560/1; 560/129
(58) Field of Search ........................... 554/1, 124, 174; 560/1, 129; 552/540

(56) References Cited

U.S. PATENT DOCUMENTS 4,393,044 A    7/1983  Takada et al.
4,748,161 A    5/1988  Kimura et al.
5,502,045 A    3/1996  Miettinen et al.
5,892,068 A    4/1999  Higgins, III

FOREIGN PATENT DOCUMENTS

EP    0 585 071 A    2/1994
EP    0 982 316 A2   3/2000

OTHER PUBLICATIONS

Delplanque et al., "Inérét nutritionnel des huiles d'olive", *Dossler*, Jan./Feb. 1999, pp. 86–93, vol. 6, No. 1.

Ling et al., "Minireview Dietary Phytosterols: A Review of Metabolism, Benefits and Side Effects", *Life* Sciences, 1995, pp. 195–206, vol. 57, No. 3, Elsevier Science Ltd.

Wachter et al., "Phytosterols, Active substances of vegetable origin in cosmetics", *Cosmetics & Toiletries Magazine*, Jul. 1995, pp. 72–82, vol. 110, Allured Publishing Corp.

*Primary Examiner*—Alton N. Pryor
(74) *Attorney, Agent, or Firm*—Foley & Lardner LLP

(57) ABSTRACT

The invention concerns a method for preparing a fatty substance ester, characterised in that it consists in subjecting to an esterification reaction at least a fatty substance with at least an alcohol compound selected from the group consisting of sterols, stanols, 4-methylsterols and their hydrogenated homologous, triterpene alcohols and their hydrogenated homologues, and mixtures thereof, in the presence of at least a solid catalyst selected in the group consisting of lanthanide oxides and the mixtures of said oxides. Said method enables to obtain products particularly suited for use in the field of pharmaceutics, in particular dermatology, cosmetics and special food production (functional food products, medicinal food products and dietetic food products)

29 Claims, No Drawings

METHOD FOR PREPARING A FATTY SUBSTANCE ESTER AND USE THEREOF IN PHARMACEUTICS, COSMETICS OR FOOD INDUSTRY

Method for preparing a fatty substance ester and use thereof in pharmaceutics, cosmetics or food industry.

The present invention relates to a novel process for the preparation of an ester of fatty substance and of an alcohol chosen from the group consisting of sterols, stanols, 4-methylsterols and their hydrogenated homologs, triterpene alcohols and their hydrogenated homologs, and the mixtures of these, this ester being intended in particular for a pharmaceutical use, in particular a dermatological use, and for a cosmetic or food use.

Phytosterols (family of the phytohormones) and essential fatty acids are compounds with a high biological activity which are therefore advantageous [lacuna] the fields of pharmaceuticals, cosmetics and the human diet.

Phytosterols are compounds of terpene origin which constitute the major fraction of plant unsaponifiable materials, an example of which is β-sitosterol. Since the 50s, phytosterols have been known in particular for their hypocholesterolemic action (Ling & Jones (1995), Life Sciences, Vol. 57, No. 3, pp. 195–206). The hypothesized mechanism of action is as follows: phytosterols lead to a decrease in the blood cholesterol by competing with the latter for its dissolution within the micelles of the bile salts in the intestine. In addition, the sterols lead to a decrease in the blood cholesterol (LDL) and a slight increase in the synthesis and excretion of endogenous cholesterol.

In an analogous way, polyunsaturated fatty acids (PUFAs) play an essential role at the nutritional level. By way of example, linoleic acid is an essential compound to the body since the latter cannot synthesize it (Delplanque et al. (1999), Oléagineux Corps Gras Lipides [Oleaginous Lipid Fatty, Substances], Vol. 1, pp. 86–93). It is in fact the starting member of the metabolic series of the n-6 or ω-6 PUFAs, fatty acids which are vital to the body. This series of acids comprises in particular arachidonic acid (C20:4), which is at the basis of the synthesis of chemical mediators, such as eicosanoids, which control numerous functions of the body, in particular platelet aggregation, the renal function and the immune response. Mention may also be made, among essential fatty acids, of eicosapentaenoic acid (EPA) and docosahexaenoic acid (DHA), for their preventive role with respect to cardiovascular diseases and some cancers.

Finally, at the dermocosmetic level, sterols and essential fatty acids are also essential compounds. Sterols are known for their antiinflammatory and antierythematous properties, in addition to their soothing and restructuring action (Wachter, Salka, Magnet, Cosmetics & Toiletries, (1995), Vol. 110, pp. 72–80). Furthermore, by limiting transepidermal water losses, mono- and polyunsaturated fatty acids for their part have a moisturizing and nutritional action. Finally, sterols and PUFAs have an important role in the synthesis of the lipids of the epidermal cutaneous barrier.

With the aim of increasing the bioavailability of sterols, and of stanols, their saturated homologs, it is known in the prior art to increase the lipophilicity of these compounds by subjecting them to an esterification reaction with a fatty substance, in particular a fatty acid or a derivative of the latter, preferably in the presence of a catalyst.

Currently, sterols and stanols are esterified by a transesterification reaction in the presence of homogeneous basic catalysts, such as sodium methoxide. The presence of NaOMe necessitates additional stages in which the catalyst in destroyed, leading to the formation of salts which it is absolutely essential to destroy. All these latter operations represent a very high additional coat in the production of these esters of sterols and of stanols. Furthermore, the use of homogeneous catalysts can promote side reactions in which the compounds are decomposed, the effect of which may be to modify the final appearance of the product (color and/or smell).

Heterogeneous catalysis, in comparison with homogeneous catalysis, exhibits the advantage of employing catalysts which can be more easily separated from the reaction medium and of creating fewer problems of corrosion and of side reactions. Mention may thus be made of magnesium oxide, which, however, exhibits the disadvantage of causing dehydration side reactions and/or reactions in which unsaturated bonds are isomerized, which reactions are unacceptable, in particular in the case of products intended for food use.

It has now been found, entirely surprisingly and unexpectedly, that the use of a certain class of compounds makes it possible to obtain an excellent heterogeneous catalysis effect for the esterification reaction involving at least one fatty substance and at least one sterol and/or one stanol and/or one 4-methylsterol, or a hydrogenated homolog of the latter, and/or one triterpene alcohol, or a hydrogenated homolog of the latter. The fatty substance esters obtained by the process according to the invention are very particularly suitable for the sectors of pharmaceuticals, in particular dermatology, cosmetics and specialized food (functional foods, medicinal foods, cosmetic foods).

The present invention thus relates to a process for the preparation of a fatty substance ester, characterized in that at least one fatty substance is subjected to an esterification reaction with at least one alcohol compound chosen from the group consisting of sterols, stanols, 4-methylsterols and their hydrogenated homologs, triterpene alcohols and their hydrogenated homologs, and mixtures of these, in the presence of at least one solid catalyst chosen from the group consisting of oxides of lanthanide metals and mixtures of these oxides.

The term "solid catalyst" is understood to mean, according to the invention, a catalyst which is undissolved in the remainder of the liquid reaction medium and which can be recycled after use.

The term "lanthanide oxide" is understood to mean, according to the invention, an oxide chosen from the group consisting of lanthanum oxide, cerium oxides, praseodymium oxides, neodymium oxides, promethium oxides, samarium oxides, europium oxides, gadolinium oxides, terbium oxides, dysprosium oxides, holmium oxides, erbium oxides, thulium oxides, ytterbium oxides, lutenium oxides and mixtures of these oxides.

The solid catalyst is preferably chosen from the group consisting of lanthanum oxide $La_2O_3$, ceric oxide $CeO_2$, praseodymium oxides $PrO_2$, $Pr_6O_{11}$ and $Pr_2O_3$, samarium oxide $Sm_2O_3$ and mixtures of these oxides.

More particularly, the solid oxide is preferably lanthanum oxide $La_2O_3$.

The solid catalyst can be provided in particular in a solid form chosen from the group consisting of powders, grains (pellets), beads, extruded forms and mixtures of these.

Preferably, the solid catalyst is in the form of a powder having a mean particle size of in particular between 1 and approximately 1000 micrometers, more particularly between approximately 10 and approximately 500 micrometers and very particularly preferably between approximately 50 and approximately 100 micrometers.

The solid catalyst can be supported on an inert support, that is to say a support which is inert in the presence of the reactants and products of the esterification reaction, such as the porous or nonporous inert supports known to a person skilled in the art, for example alumina or silica.

The oxides of lanthanides used as catalysts in the process according to the invention can be prepared according to methods known to a person skilled in the art, including when a supported catalyst is involved. They are also commercially available, such as the "LSA" and "HSA" forms sold by Rhodia.

The weight of catalyst to be used in the process according to the invention can be determined by a person skilled in the art using his overall knowledge, in particular with regard to the esterification reaction.

In particular, the solid catalyst used in the process according to the invention is present in the reaction medium in a proportion of between approximately 0.01 and approximately 30% by weight and more particularly between 1 and 5% by weight, with respect to the total weight of the reaction medium.

The esterification reaction employed in the process according to the invention can be any esterification reaction in which one of the starting reactants is a sterol and/or a stanol and/or a 4-methylsterol, or a hydrogenated homolog of the latter, and/or a triterpene alcohol, or a hydrogenated homolog of the latter, such as the direct esterification reaction between these alcohol compounds and a carboxylic acid or its acid chloride or anhydride or alternatively the transesterification reaction by alcoholysis between these alcohol compounds and an ester.

The term "fatty substance" is understood to mean, according to the invention, in agreement with the overall knowledge of a person skilled in the art, a molecule comprising, first, at least one chemical functional group which can react with an alcohol compound in an esterification reaction as described above, in particular a carboxylic acid, acid chloride, acid anhydride or, in the case of a transesterification by alcoholysis, an ester functional group. Secondly, the molecule of the fatty substance comprises at least one "fatty" hydrocarbonaceous chain, that is to say a linear hydrocarbonaceous chain of at least 7 carbon atoms which is saturated or unsaturated and optionally substituted, in particular a linear $C_7$–$C_{30}$ hydrocarbonaceous chain. The fatty chain is preferably a linear, ethylenically unsaturated, $C_7$–$C_{30}$ hydrocarbonaceous chain comprising at least one ethylenic unsaturation. More particularly, the fatty chain is a linear, ethylenically unsaturated, $C_7$–$C_{30}$ hydrocarbonaceous chain comprising at least two conjugated or nonconjugated ethylenic unsaturations, such as, for example, in the case of methyl linoleate.

In particular, the fatty substance is chosen from the group consisting of saturated fatty acids, in particular capric acid, lauric acid, stearic acid, or also myristic acid, palmitic acid and mixtures of these, and unsaturated fatty acids, in particular undecylenic acid, oleic acid, ricinoleic acid, linoleic acid, or also ω-3 acids, such as linolenic acid and those of formulae:

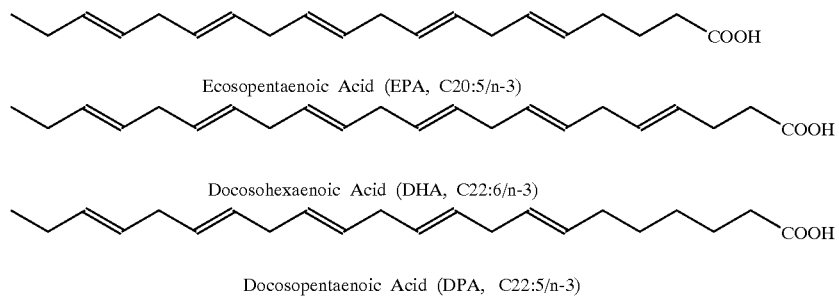

Ecosopentaenoic Acid (EPA, C20:5/n-3)

Docosohexaenoic Acid (DHA, C22:6/n-3)

Docosopentaenoic Acid (DPA, C22:5/n-3)

Docosopentaenoic Acid (DPA, C22:5/n-3) and the mixtures of these.

Mention will also be made, among fatty acids which can be used as fatty substances for these esterification reactions, of in particular the fatty acids obtained from fatty acid soaps which are byproducts from the saponification of a vegetable oil or from the refining of oils (soap stocks). This is because this represents a very advantageous enhancement in value of these byproducts from the preparation of vegetable oil unsaponifiable materials.

Mention may in particular be made, among vegetable oils which can be used, of sunflower oil, palm oil, palm kernel oil, coconut oil, grape seed oil, black mustard oil, poppyseed oil, karite butter oil, sweet almond oil, soybean oil, avocado oil, lupin oil, groundnut oil, cottonseed oil, sesame oil, olive oil, corn oil, cocoa oil, castor oil, ben oil, linseed oil, rapeseed oil, annatto oil, wheat germ oil, safflower oil, walnut oil, hazelnut oil, rapeseed oil, rice bran oil and mixtures of these oils.

The saponification of the oil, in particular of avocado oil (or soybean oil), is an essential stage in the process for producing the unsaponifiable materials. This stage, carried out in the presence of aqueous potassium hydroxide and of ethanol, is a basic hydrolysis of the oil (triglycerides), resulting in the formation of potassium soaps and of glycerol:

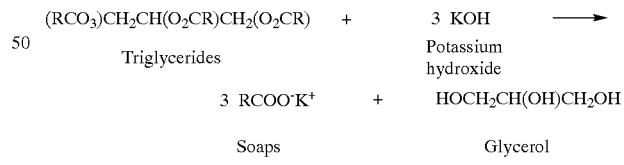

The unsaponifiable material, as an emulsion in the aqueous/alcoholic phase ("soapy" phase), is subsequently extracted with dichloroethane (DCE) according to a liquid-liquid extraction process.

After the stage of liquid-liquid extraction, the "soapy" phase is acidified with sulfuric acid. The soaps are then converted to fatty acids (reaction 1 below). The mixture obtained is subsequently distilled in order to remove the ethanol and the traces of DCE. The fatty acids and the water are finally separated by settling.

$$2\ RCOO^-K^+ + H_2SO_4 \rightarrow 2\ RCOOH + K_2SO_4 \qquad (1)$$

These crude avocado fatty acids are finally purified, for example on a silica column (eluent: hexane then hexane/diethyl ether 95/5) or by molecular distillation, and can thus constitute the starting material used during the preparation of fatty esters of avocado and of sterol and/or of stanol [lacuna], or of a hydrogenated homolog of the latter, and/or of triterpene alcohol, or of a hydrogenated homolog of the latter, according to the process of the present invention.

Soybean fatty acids or fatty acids of another vegetable oil, such as those mentioned above, can be obtained according to the same synthetic group.

Thus, according to a specific embodiment, the fatty substance esterified according to the invention is a fatty acid from at least one hydrogenated or non-hydrogenated vegetable oil, it being understood that the expression "vegetable oil fatty acid" encompasses, according to the invention, the fatty acids originally present in said vegetable oil and the fatty acids which can be obtained by treatment of the soapy phase after saponification of said vegetable oil, as described above.

Finally, the fatty substance esterified according to the invention, in the case of an esterification by alcoholysis (transesterification), can be an ester of a fatty acid, such as the fatty acids described above, in particular an ester in which the alkyl part of the alkoxy group is a $C_1$–$C_{22}$ alkyl part, for example an ethylhexyl part, and more particularly a $C_1$–$C_6$ alkyl part, such as the methyl, ethyl, propyl, isopropyl, butyl, tert-butyl, pentyl or hexyl group, and more particularly still a $C_1$–$C_3$ alkyl part.

Mention may in particular be made of methyl laurate, methyl myristate or also methyl oleate, methyl linoleate, methyl stearate, methyl undecylenate, butyl oleate, methyl ricinoleate, methyl palmitate or also methyl palmitoelate, and the mixtures of these.

Advantageously, the fatty substance esterified according to the invention can be in the form of at least one hydrogenated or nonhydrogenated vegetable oil comprising fatty acids and/or fatty acid esters, such as the vegetable oils already mentioned above, or a mixture of these hydrogenated or nonhydrogenated oils.

The alcohol compound used in the process according to the invention is chosen from the group consisting of sterols, stanols, 4-methylsterols and their hydrogenated homologs, triterpene alcohols and their hydrogenated homologs, and the mixtures of these.

The sterols and stanols used as starting material in the process according to the invention are compounds well known to a person skilled in the art.

The term "sterol" is understood to mean more particularly, according to the invention, sterol, that is to say the compound perhydro-1,2-cyclopentano-phenanthrene having a hydroxyl group at the 3-position, and the sterol analogs of general formula (I) below.

The term "stanol" is understood to mean, according to the invention, the derivative hydrogenated at the 5-position of a given sterol as defined above.

Thus, preferably, the sterols and stanols which can be used as starting materials in the process according to the invention correspond to the following general formula:

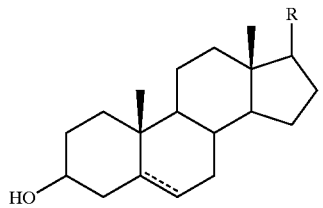

in which the unsaturation marked by a dotted line in the 5-position corresponds to the unsaturation in the case of sterols and R represents a saturated or unsaturated and linear or branched hydrocarbonaceous chain comprising from 1 to 25 carbon atoms. In particular, R is chosen from the group consisting of $C_1$–$C_{12}$ alkyl groups, $C_1$–$C_8$ alkoxy group, $C_2$–$C_8$ alkenyl groups, $C_2$–$C_8$ alkynyl group, $C_3$–$C_8$ cycloalkyl groups, halogenated $C_2$–$C_8$ alkenyl groups and halogenated $C_2$–$C_8$ alkynyl groups. The term "halogenated" denotes one or more halogen substituent, namely one or more chlorine, fluorine, bromine or iodine atom(s).

Mention may in particular be made, among the sterols which can advantageously be used in the process according to the invention, of β-sitosterol, α-sitosterol, γ-sitosterol, stigmasterol or campesterol, and the mixtures of these. For example, β-sitosterol can be used in the form of the product known as "Ultra" (mainly comprising β-sitosterol) as sold by Kaukas. In the case of use of a mixture of sterols, mention may be made, for example, of the product known as "Generol", mainly comprising β-sitosterol (approximately 50% by weight), stigmasterol and campesterol, as sold by Henkel or the product "Primal" from Kaukas.

Mention may in particular be made, among the stanols which can advantageously be used in the process according to the invention, of β-sitostanol, stigmastanol or campestanol, and the mixtures of these. Of course, as is well known to a person skilled in the art, the stanols used in the process according to the invention can be obtained by catalytic hydrogenation of sterols, such as the abovementioned sterols, for example during a stage upstream of the esterification stage according to the invention, one using well-known catalysts, such as palladium, platinum, copper or nickel.

4-Methylsterols, as described in particular in the "Manuel des Corps Gras" [Handbook of Fatty Substances], published by Tec&Doc Lavoisier under the aegis of the Association Française pour l'Etude des Corps Gras [French Association for the Study of Fatty Substances] (1992 edition, Alain Karleskind and Jean-Pierre Wolff), have as biosynthetic origin cycloartenol and 24-methylenecycloartanol in plants and lanosterol in animals; they are characterized by the presence of a single methyl group in the 4a position, the other having been subjected to oxidative decomposition and removal in the form of carbon dioxide (Benveniste, 1986). The methyl group in the 14a position may either remain or be removed in the form of formic acid and replaced by a hydrogen atom. The cyclopropane ring in the 9-10-19 position may be maintained or else may be subjected to opening, giving rise to the 19 methyl group and to a double bond located in the 9(11) or in the 8(9) position. The usual nomenclature uses the name of the related triterpene alcohol, preceded by "3l-nor"; the systematic nomenclature is based on the name of the related sterol, preceded by "4α-methyl".

The 4-methylsterols which can be used as alcohol compound in the process according to the invention are in particular those of following formula (II):

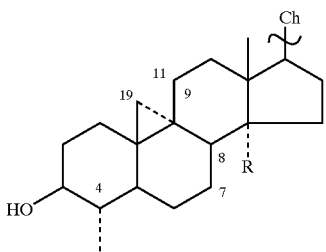

in which the substituent Ch represents a group having one of the following formulae a to h:

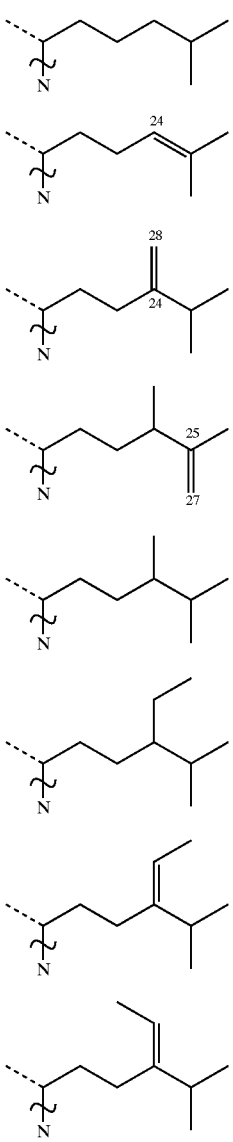

4-Methylsterols corresponding to this formula (II) and which can very particularly be used, alone or in the form of a mixture of the latter, as alcohol compound in the process according to the invention are mentioned in the following table 1.

TABLE 1

| Name | R | Δ | Ch |
|---|---|---|---|
| 31-Norcycloartanol | Me | 9(19) | a |
| 31-Norcycloartenol | Me | 9(19) | b |
| Cycloeucalenol | Me | 9(19) | c |
| 31-Norcyclolaudenol | Me | 9(19) | d |
| 31-Norlanosterol | Me | 8(9) | a |
| 24 (28)-Dihydroobtusifoliol | Me | 8(9) | e |
| Obtusifoliol | Me | 8(9) | c |
| 31-Norparkeol | Me | 9(11) | b |
| 4a-Methylergosta-8,24-dien-3β-ol | H | 8(9) | c |
| Lophenol | H | 7(8) | a |
| 4a-Methylcholesta-7,24-dien-3β-ol | H | 7(8) | b |
| (24R)-24-Methyllophenol | H | 7(8) | e |
| 24-Methylenelophenol | H | 7(8) | c |
| 24-Ethyllophenol | H | 7(8) | f |
| Citrostadienol | H | 7(8) | g |
| Isocitrostadienol | H | 7(8) | h |

The term "hydrogenated homologs" of a 4-methylsterol is understood to mean, according to the invention, the corresponding 4-methylsterol compound or compounds in which the unsaturated bond or bonds which may be present have been hydrogenated (that is to say, converted to a saturated bond) according to methods well known to a person skilled in the art.

Mention may in particular be made among the triterpene alcohols which can advantageously be used in the process according to the invention, of β-amyrin, erythrodiol, taraxasterol, cycloartenol, 24-methylene-cycloartanol, lanosterol and the mixtures or these.

The term "hydrogenated homologs" of a triterpene alcohol is understood to mean, according to the invention, the corresponding triterpene alcohol compound or compounds in which the unsaturated bond or bonds which may be present have been hydrogenated (that is to say, converted to a saturated bond) according to methods well known to a person skilled in the art.

The molar ratios of the reactants for the process according to the invention are such that use is made in particular of a fatty substance:alcohol compound molar ratio of between approximately 0.5 and approximately 50 and more particularly between approximately 1 and approximately 2.

The temperature of the esterification reaction according to the invention is preferably between approximately 100 and approximately 400° C. and more particularly between approximately 200 and approximately 250° C. The pressure can be between approximately 0.05 and approximately 50 bar and more particularly between approximately 0.1 and approximately 5 bar. In order to avoid possible oxidation of the ethylenic bonds present, it is recommended either to purge the reaction medium and the reactants with an inert gas or to carry out the reaction under a stream of inert gas or a partial vacuum or to carry out the reaction under a pressure of inert gas of between approximately 0.1 and approximately 5 bar.

Although the process according to the invention can advantageously be carried out in the absence of solvent, it is possible, if appropriate, in particular when the alcohol is soluble with difficulty in the fatty substance, to use a solvent preferably chosen from the group consisting of alkanes, halogenated alkanes (in particular chlorinated alkanes), dimethylformamide (DMF) or dimethyl sulfoxide (DMSO).

By the process according to the invention, the esterification reaction results in the production of an ester exhibiting entirely acceptable organoleptic qualities (smell, color, taste), a low acid number and a minimal content of free alcohol.

Of course, the process according to the invention can additionally comprise the stages upstream or downstream of a catalyzed esterification reaction which are known to a person skilled in the art.

In particular, the purity of the product obtained can be further improved, for example by decoloration, deodorization or molecular distillation.

Furthermore, the use of solid lanthanide oxides as solid catalyst makes possible the use of an industrial process which is less damaging to the environment (saving of energy, recycling of the catalyst, byproducts and effluents and the complete absence of solvents), insofar as these oxides are particularly easy to recover and can be recycled, in comparison with the currently known catalysts for esterification of sterols, stanols, 4-methylsterols and triterpene alcohols, which require in particular their destruction with formation of salts.

Thus, by an appropriate choice of the pharmaceutical quality, in particular dermatological quality, cosmetic quality and/or food quality of the starting reactants, by using the overall knowledge of a person skilled in the art and by the improved separation of the catalyst from the reaction product at the end of the esterification, the process according to the invention makes it possible to obtain products which are particularly suited to use in the fields of pharmaceuticals, in particular dermatology, cosmetics and specialized food (functional foods, medicinal foods, cosmetic foods).

Thus, another subject matter of the present invention is the use of at least one fatty substance ester as obtained by the esterification process described above as pharmaceutically active agent, in particular dermatological agent, in a pharmaceutical composition, in particular a dermatological composition.

In addition, another subject matter of the present invention is the use of at least one fatty substance ester as obtained by the esterification process described above as cosmetically active agent in a cosmetic composition.

Finally, another subject matter of the present invention is the use of at least one fatty substance ester as obtained by the esterification process described above as food additive.

The following examples are intended to illustrate the present invention but should under no circumstances be interpreted as being able to restrict the scope thereof.

EXAMPLE 1

Use of Lanthanum Oxide for the Transesterification of Methyl Esters with a Mixture of Sterols 1) Characteristics of the Reactants The mixture of sterols used is mainly composed of β-sitosterol, at approximately 50%. A detailed analysis of this mixture, sold by Henkel under the name "Generol", gives the following results (see table 2):

TABLE 2

| Product | Composition |
| --- | --- |
| Campesterol | 26 to 31% |
| Campestanol | Traces |
| Stigmasterol | 16 to 23% |
| β-Sitosterol | 48 to 53% |
| β-Sitostanol | Traces |

This mixture will subsequently be denoted by "sterols of the mixture A".

The methyl esters used are as follows:
- the methyl laurate is of industrial origin; after analysis, its purity is at least 98%;
- the methyl myristate and the methyl oleate are commercial industrial products, the respective oleate and myristate purities of which are 87% and 99% by weight.

In each product, the remainder to 100% is composed of other methyl esters with a shorter or longer chain than that of the oleate or myristate esters respectively predominant.

2) Procedure

The transesterification reaction is carried out at atmospheric pressure in a 250 ml 4-necked pyrex reactor. The characteristics of the assembly are as follows:

heating via a heating mantle with adjustment of the temperature;

mechanical stirring;

nitrogen inlet;

thermometer pocket, allowing the temperature to be measured using a thermocouple;

outlet of the reactor, equipped with a reflux condenser, in order to make possible the removal of the methanol formed, which methanol is collected in a collecting trap.

29 g of the mixture of sterols are introduced into the reactor, along with a mass of methyl ester such that a molar ratio of the reactants of 1 (i.e. 15 g of methyl laurate, for example) is achieved.

The reactants are stirred at 500 rev/min and are gradually heated to the temperature of 240° C.

Once the reaction temperature has been reached, at time t=0, three drops of reaction mixture are withdrawn with a Pasteur pipette. This withdrawn sample will be the reference for all the calculations.

2.316 g of lanthanum oxide $La_2O_3$, sold by Rhodia under the name "HSA", are then introduced as solid catalyst.

This therefore corresponds to 5% by weight of catalyst with respect to the total weight of the reaction mixture. The lanthanum oxide is in the form of a powder with a particle size such that the mean particle size is approximately 75 micrometers.

Finally, nitrogen is introduced into the assembly with a flow rate of 80 ml/min, the nitrogen sweeping the surface of the reaction mixture and making it possible to entrain the methanol formed during the transesterification reaction toward the collecting trap.

Withdrawn samples are taken over time, t=0, 0.5, 1, 2, 3, 5 and 7 hours. These samples are weighed exactly and are then dissolved in 1 ml of a solution of hexadecane (internal standard) in dodecane, in a proportion of 3.2 mmol of standard per 50 ml of dodecane. The dodecane, used here as solvent, and the hexadecane, the internal standard, are respectively Sigma and Merck products; their purity is 99%. The sample thus prepared is quantitatively determined by gas chromatography using a Varian 3350 chromatograph equipped with a flame ionization detector and an on-column injector. The products are separated using an SGE BP5 capillary column.

The total duration of the reaction is 7 hours.

3) Use of the Results 3.1 Definition and Expression of the Conversion

As each withdrawn sample is dissolved in 1 ml of solution of hexadecane diluted in dodecane, there is therefore a precise and constant amount of hexadecane present, i.e. $N_h = 6.1 \times 10^{-5}$ mol.

Thus, the analyses give us the areas of the products and of the reactants but also that of our standard. As the response factors of each of the entities, factors determined with respect to the hexadecane, are known, it is therefore possible to easily determine the amounts of reactants and of products present in a mass $m_t$ of a withdrawn sample taken at a time t.

The first withdrawn sample with a mass $m_o$ allows us to determine the theoretical amount of a reactant A at time t=0:

$$Nth_{ao} = \frac{S_{a0} * N_h}{f_a * S_{h0}}$$

(Nth$_{a0}$ and N$_h$ in mol)

S$_{a0}$ and S$_{h0}$ are the areas of the reactant A and of the standard recorded on conclusion of the analysis of the withdrawn sample taken at t=0 and f$_a$ is the response factor of the reactant A.

Likewise, at time t=t, the amount of reactant A present in a withdrawn sample with a mass m$_t$ is expressed thus:

$$N_{at} = \frac{S_{at} * N_h}{f_a * S_{ht}}$$

If the reactant A had not been consumed since time t=0, there would be in reality a theoretical amount Nth$_{at}$ expressed in the following way:

$$Nth_{at} = \frac{Nth_{a0} * m_t}{m_0}$$

(Nth$_{at}$ and Nth$_{a0}$ in mol, m$_0$ and m$_t$ in g)

The conversion of the reactant A is therefore defined as being the ratio of the amount of reactant consumed to the theoretical amount of reactant: % conversion A=100

$$\frac{Nth_{at} - N_{at}}{Nth_{at}}$$

3.2 Definition and Expression of the Selectivity of a Product

The selectivity of a product is the ratio of the amount of this product to the sum of the amounts of the products present in the withdrawn sample.

In the present case, as esters of sterols, dienes and unidentified byproducts (which will be given the name "others" here) are formed, the following expression is obtained:

$$\% \text{ selectivity esters} = 100 \frac{N_{esters_t}}{N_{esters_t} + N_{dienes_t} + N_{others_t}} (N \text{ in mol})$$

3.3 Definition and Expression of the Reaction Yield

In the present case, the reaction yield, expressed as %, is the product of the % of conversion of the sterols by the % of selectivity for esters of sterols, everything being divided by 100:

Yield (%)=(% conversion sterols*% selectivity esters)/100

4) Results 4.1 Influence of the Nature of the Catalyst: Transesterification of Methyl Laurate by the Sterols of the Mixture A 5% by weight of each catalyst, in the form of a powder with a particle size of 75 micrometers, are used. Potassium carbonate is used as reference catalyst.

TABLE 3

| Catalyst (5% by weight) | % conversion of methyl laurate | % conversion of the sterols of the mixture | Yield (%) |
|---|---|---|---|
| Catalyst-free reaction | 25 | 74 | 38 |
| Lanthanum oxide | 100 | 99 | 91 |
| Potassium carbonate | 99 | 98 | 82 |

By comparison with potassium carbonate, the use of lanthanum oxide according to the invention makes it possible to obtain a better yield of sterol ester. Furthermore, by the end of the reaction, the potassium carbonate is virtually completely dissolved in the reaction medium, which renders its reuse virtually impossible and its extraction from the reaction medium laborious (successive washings, and the like). In contrast, the lanthanum oxide can be separated directly from the reaction medium by simple filtration.

4.2 Influence of the Specific Surface of the Catalyst: Transesterification of Methyl Laurate by the Sterols of the Mixture A, Catalyzed by Lanthanum Oxide

TABLE 4

| Specific surface of the lanthanum oxide (m$^2$/g) | % conversion of methyl laurate | % conversion of the sterols of the mixture | Yield (%) |
|---|---|---|---|
| 1 | 47 | 59 | 53 |
| 68 | 94 | 99 | 92 |

4.3 Influence of the Amount of Catalyst: Transesterification of Methyl Laurate by the Sterols of the Mixture A

TABLE 5

| Percentage by mass | % conversion of methyl lanrate (1) | % conversion of the sterols of the mixture | Yield (%) |
|---|---|---|---|
| 5 | 47 | 59 | 53 |
| 10 | 81 | 88 | 81 |

(1) Reaction time of 7 hours 4.4 Influence of the Reaction Temperature: Transesterification of Methyl Laurate by the Sterols of the Mixture A

TABLE 6

| Temperature (° C.) | % conversion of methyl laurate (1) | % conversion of the sterols of the mixture | Yield (%) |
|---|---|---|---|
| 220 | 66 | 92 | 67 |
| 230 | 97 | 96 | 90 |
| 240 | 100 | 99 | 91 |

(1) Reaction time of 7 hours 4.5 Influence of the Nature of the Methyl Ester: Transesterification of Various Esters by the Sterols of Mixture A

TABLE 7

| Ester | % conversion of the ester | % conversion of the sterols of the mixture | Yield (%) |
|---|---|---|---|
| Methyl laurate | 100 | 99 | 91 |
| Methyl myristate | 90 | 99 | 87 |
| Methyl oleate | 100 | 99 | 86 |

4.6 Transesterification of the Esters of Sunflower Oil by the Sterols of the Mixture A

TABLE 8

| % conversion sunflower oil | % conversion of the sterols of the mixture | Yield of esters of sterols (%) |
|---|---|---|
| 100 | 99 | 73 |

EXAMPLE 2

Comparison with the Magnesium Oxide Solid Catalyst

An experiment is carried out in the presence of MgO under the same operating conditions as for example 1 except for the reaction time, which is 5 hours. In particular, the magnesium oxide is in the form of a powder with a similar particle size to that of the lanthanum oxide, which is the same as that used in example 1. The results are listed in the following table 9.

It is found that, in the presence of magnesium oxide, the ester formed from methyl laurate and from β-sitosterol is rapidly decomposed to give other products. Furthermore the high basicity of magnesium oxide doped with alkali metal elements promotes the reaction for the dehydration of β-sitosterol.

TABLE 9

| Solid catalyst | % Conv. Laurate | % Conv. Sterols | % Dienes | % Esters | % Others | Yield |
|---|---|---|---|---|---|---|
| $La_2O_3$ | 100 | 95 | 1 | 95 | 4 | 90 |
| MgO | 97.8 | 95.1 | 9 | 82 | 9 | 78 |

Reaction time: 5 hours

EXAMPLE 3

Recycling Capability of the Lanthanum Oxide $La_2O_3$ Solid Catalyst

Four identical tests are carried out in succession on the esterification reaction in a reactor in the presence of the same $La_2O_3$ solid catalyst as for examples 1 and 2. At the end of each tests, the catalyst is separated from the reaction medium by simple settling and filtration and then the solid catalyst thus recovered is reintroduced into the reactor with a fresh charge of reactants (sterols and methyl laurate). The results are listed in the following table 10 for the first reaction and the three other following reactions denoted by "recycling". It is found that the yields are not significantly modified, even after several operating cycles. These tests clearly show the advantageous use of the lanthanum oxide solid catalyst for its ease of separation from the reaction product and, what is more, its recycling capability.

TABLE 10

| Reaction | % Conv. Laurate | % Conv. Sterols | % Dienes | % Esters | % Others | Yield |
|---|---|---|---|---|---|---|
| 1st Reaction | 100 | 95 | 1 | 95 | 4 | 90 |
| 1st Recycling | 97 | 99 | 1 | 96 | 3 | 95 |
| 2nd Recycling | 96 | 99 | 1 | 94 | 5 | 93 |
| 3rd Recycling | 94 | 98 | 1 | 93 | 6 | 91 |

Reaction time: 5 hours

What is claimed is:

1. A process carried out in a reaction medium for the preparation of a fatty substance ester, comprising subjecting at least one fatty substance to an esterification reaction with at least one alcohol compound chosen from the group consisting of sterols, stanols, 4-methylsterols and their hydrogenated homologs, triterpene alcohols and their hydrogenated homologs, and mixtures of these, in the presence of at least one solid catalyst chosen from the group consisting of oxides of lanthanide metals and mixtures of these oxides.

2. The process as claimed in claim 1, wherein the solid catalyst is chosen from the group consisting of lanthanum oxides, cerium oxides, praseodymium oxides, neodymium oxides, promethium oxides, samarium oxides, europium oxides, gadolinium oxides, terbium oxides, dysprosium oxides, holmium oxides, erbium oxides, thulium oxides, ytterbium oxides, lutenium oxides and mixtures of these oxides.

3. The process as claimed in claim 1, wherein the solid catalyst is chosen from the group consisting of lanthanum oxide $La_2O_3$, ceric oxide $CeO_2$, praseodymium oxides $PrO_2$, $Pr_6O_{11}$ and $Pr_2O_3$, samarium oxide $Sm_2O_3$ and mixtures of these oxides.

4. The process as claimed in claim 1, wherein the solid catalyst is lanthanum oxide $La_2O_3$.

5. The process as claimed in claim 1, wherein the solid catalyst is provided in a solid form chosen from the group consisting of powders, grains, pellet, beads, extruded forms and mixtures of these.

6. The process as claimed in claim 1, wherein the solid catalyst is in the form of a powder with a mean particle size of between approximately 1 and approximately 1,000 micrometers.

7. The process as claimed in claim 1, wherein the solid catalyst is supported on an inert support.

8. The process as claimed in claim 1, wherein the solid catalyst is present in the reaction medium in a proportion of between approximately 0.01 and approximately 30% by weight with respect to the total weight of the reaction medium.

9. The process as claimed in claim 1, wherein the fatty substance comprises at least one optionally substituted, saturated or unsaturated linear $C_7$–$C_{30}$ hydrocarbonaceous chain.

10. The process as claimed in claim 9, wherein the fatty substance comprises at least one linear, ethylenically unsaturated, $C_7$–$C_{30}$ hydrocarbonaceous chain comprising at least one ethylenic unsaturation.

11. The process as claimed in claim 9, wherein the fatty substance comprises at least one linear, ethylenically unsaturated, $C_7$–$C_{30}$ hydrocarbonaceous chain comprising at least two conjugated or nonconjugated ethylenic unsaturations.

12. The process as claimed in claim 1, wherein the fatty substance is a saturated fatty acid chosen from the group consisting of capric acid, lauric acid, stearic acid, myristic acid, palmitic acid and the mixtures of these.

13. The process as claimed in claim 1, wherein the fatty substance is an unsaturated fatty acid chosen from the group consisting of undecylenic acid, oleic acid, ricinoleic acid, linoleic acid, ω-3 acids, linolenic acid,

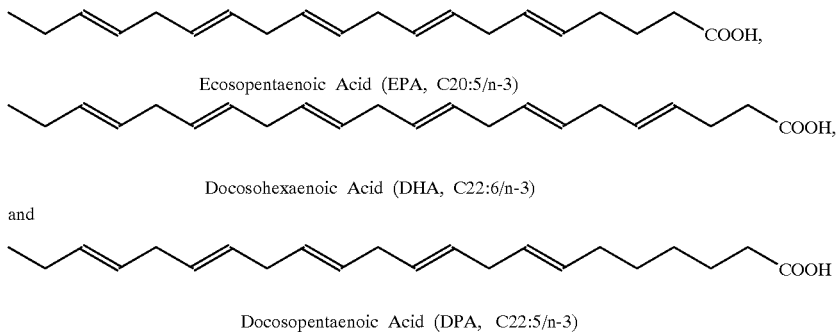

and mixture thereof.

14. The process as claimed in claim 1, wherein the fatty substance is a fatty acid of at least one hydrogenated or nonhydrogenated vegetable oil.

15. The process as claimed in claim 1, wherein the fatty substance is an ester of a fatty acid.

16. The process as claimed in claim 15, wherein the fatty acid is chosen from the group consisting of capric acid, lauric acid, stearic acid, myristic acid, palmitic acid and mixtures thereof.

17. The process as claimed in claim 15, wherein the fatty acid is chosen from the group consisting of undecylenic acid, oleic acid, ricinoleic acid, linoleic acid, ω-3 acids, linolenic acid and those of formulae:

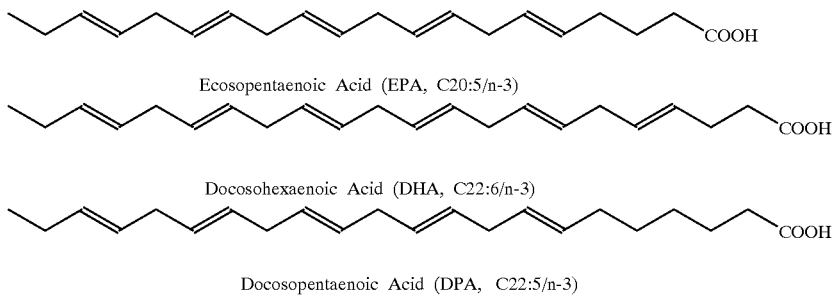

and mixtures thereof.

18. The process as claimed in claim 15, wherein the fatty acid is of at least one hydrogenated or nonhydrogenated vegetable oil.

19. The process as claimed in claim 15, wherein the fatty substance is a fatty acid ester chosen from the group consisting of methyl laurate, methyl myristate, methyl oleate, methyl linoleate, methyl stearate, methyl undecylenate, butyl oleate, methyl ricinoleate, methyl palmitate, methyl palmitoelate and mixtures thereof.

20. The process as claimed in claim 1, wherein the fatty substance is a hydrogenated or nonhydrogenated vegetable oil or a mixture of hydrogenated or nonhydrogenated vegetable oils.

21. The process as claimed in claim 14, wherein the vegetable oil is chosen from the group consisting of sunflower oil, palm oil, palm kernel oil, coconut oil, grape seed oil, black mustard oil, poppyseed oil, karite butter oil, sweet almond oil, soybean oil, avocado oil, lupin oil, groundnut oil, cottonseed oil, sesame oil, olive oil, corn oil, cocoa oil, castor oil, ben oil, linseed oil, rapeseed oil, annatto oil, wheat germ oil, safflower oil, walnut oil, hazelnut oil, rapeseed oil, rice bran oil and mixtures thereof.

22. The process as claimed in claim 20, wherein the vegetable oil is chosen from the group consisting of sunflower oil, palm oil, palm kernel oil, coconut oil, grape seed oil, black mustard oil, poppyseed oil, karite butter oil, sweet almond oil, soybean oil, avocado oil, lupin oil, groundnut oil, cottonseed oil, sesame oil, olive oil, corn oil, cocoa oil, castor oil, ben oil, linseed oil, rapeseed oil, annatto oil, wheat germ oil, safflower oil, walnut oil, hazelnut oil, rapeseed oil, rice bran oil and mixtures thereof.

23. The process as claimed in claim 1, wherein the alcohol compound is chosen from the group of the sterols and stanols corresponding to the following general formula:

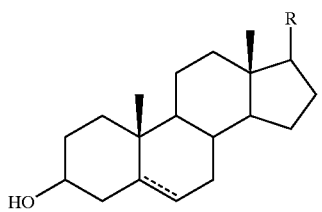

(I)

in which the unsaturation marked by a dotted line in the 5-position corresponds to the unsaturation in the case of sterols and wherein R, which represents a saturated or unsaturated and linear or branched hydrocarbonaceous chain comprising from 1 to 25 carbon atoms, is chosen from the group consisting of $C_1$–$C_{12}$ alkyl groups, $C_1$–$C_8$ alkoxy group, $C_2$–$C_8$ alkenyl groups, $C_2$–$C_8$ alkynyl group, $C_3$–$C_8$ cycloalkyl groups, halogenated $C_2$–$C_8$ alkenyl groups and halogenated $C_2$–$C_8$ alkynyl groups.

24. The process as claimed in claim 23, wherein the alcohol compound is chosen from the group consisting of β-sitosterol, α-sitosterol, γ-sitosterol, stigmasterol, campesterol, β-sitostanol, stigmastanol, campestanol and mixtures thereof.

25. The process as claimed in claim 1, wherein the alcohol compound is a 4-methylsterol chosen from the group consisting of 31-norcycloartanol, 31-norcycloartenol, cycloeucalenol, 31-norcyclolaudenol, 31-norlanosterol, 24 (28)-dihydro-obtusifoliol, obtusifoliol, 31-norparkeol, 4α-methyl-ergosta-8, 24-dien-3β-ol, lophenol, 4α-methylcholesta-7,24-dien-3β-ol, (24R)-24-methyllophenol, 24-methylenelophenol, 24-ethyllophenol, citrostadienol, isocitrostadienol and mixtures thereof.

26. The process as claimed in claim 1, wherein the alcohol compound is a triterpene alcohol chosen from the group consisting of β-amyrin, erythrodiol, taraxasterol, cycloartenol, 24-methylenecycloartanal, lanosterol and mixtures thereof.

27. The process as claimed in claim 1, wherein the fatty substance:alcohol compound molar ratio is between approximately 0.5 and approximately 50.

28. The process as claimed in claim 1, wherein the temperature of the esterification reaction according to the invention is between approximately 100 and approximately 400° C.

29. The process as claimed in claim 1, wherein the pressure is between approximately 0.05 and approximately 50 bar.

* * * * *